United States Patent

Rabenecker et al.

[11] Patent Number: 6,129,894
[45] Date of Patent: Oct. 10, 2000

[54] DEVICE FOR TAKING SWAB SAMPLES AND SAMPLE DILUTION

[75] Inventors: Horst Rabenecker, Stockelsdorf; Rainer Polzius, Lübeck; Gero Vornbäumen, Lübeck; Andreas Manns, Lübeck; Thomas Wuske, Malente, all of Germany

[73] Assignee: Dräger Sicherheitstechnik GmbH, Germany

[21] Appl. No.: 09/302,388

[22] Filed: Apr. 30, 1999

[30] Foreign Application Priority Data

Dec. 10, 1998 [DE] Germany ............... 298 22 031 U

[51] Int. Cl.[7] ............... G01N 1/18; A61M 35/00
[52] U.S. Cl. ............... 422/61; 422/99; 422/100; 422/101; 436/178; 604/1; 604/3; 604/208; 604/210
[58] Field of Search ............... 422/61, 99, 100, 422/101; 436/178, 179; 73/864.12, 864.71, 864.72; 604/1, 2, 3, 186, 187, 208, 210

[56] References Cited

U.S. PATENT DOCUMENTS

| | | | |
|---|---|---|---|
| 3,519,364 | 7/1970 | Truhan | 401/177 |
| 3,934,586 | 1/1976 | Easton et al. | 128/235 |
| 4,874,385 | 10/1989 | Moran | 604/208 |
| 5,460,611 | 10/1995 | Alexander | 604/110 |
| 5,550,061 | 8/1996 | Stone | 436/73 |
| 5,823,954 | 10/1998 | Chaffringeon | 600/367 |
| 5,833,669 | 11/1998 | Wyrick | 604/234 |

FOREIGN PATENT DOCUMENTS

| | | |
|---|---|---|
| 44 39 429 C2 | 2/1996 | Germany. |
| 198 30 405 | 1/2000 | Germany. |

*Primary Examiner*—Jill Warden
*Assistant Examiner*—Dwayne K Handy
*Attorney, Agent, or Firm*—McGlew and Tuttle, P.C.

[57] ABSTRACT

A device is provided for taking swab samples and sample dilution. The device has a plug made of a porous, absorbent material, which projects from a sleeve and is used to take a swab sample. The plug is located in one end of the sleeve. A piston, which can be moved in the sleeve by means of a piston rod, is located in the other end of the sleeve. A closure, which can be opened by means of pressure, is located between the piston and the plug, so that a liquid arranged between the piston and the plug moves through the closure to the plug and wets same on actuation of the piston rod.

15 Claims, 1 Drawing Sheet

Fig.
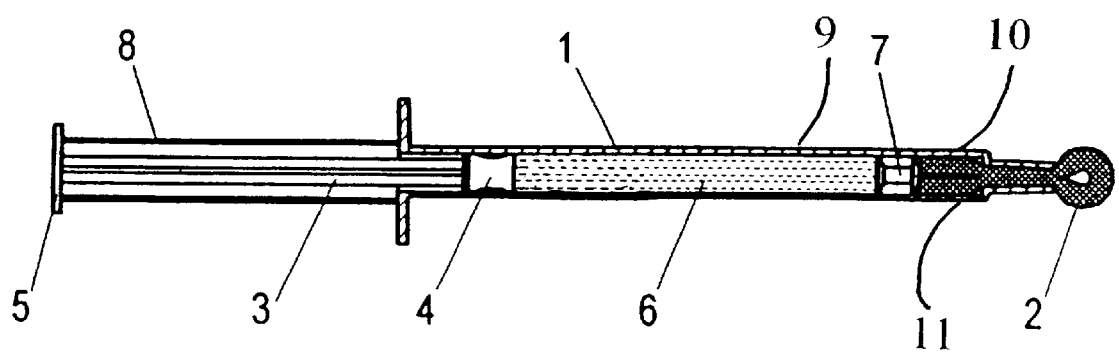

DEVICE FOR TAKING SWAB SAMPLES AND SAMPLE DILUTION

FIELD OF THE INVENTION

The present invention pertains to a device for taking swab samples and sample dilution.

BACKGROUND OF THE INVENTION

Devices that are suitable for taking swab samples from surfaces have become known in various embodiments. For example, a device with a corresponding process, in which a separate swab sampler with the swab sample is pressed in a correctly fitting manner to a detection unit and a dilution or chemical formulation of the swab sample is subsequently performed, has been known from DE 44 39 429 C2.

A process for the detection of an analyte on surfaces, in which the analyte is swabbed from the surface with a swabbing surface of an analytical test strip and a chemical or immunochemical detection reaction is subsequently carried out directly by means of the analytical test strip, has become known from the patent application DE 198 30 405.6. One drawback of this process and of the corresponding device is that after sampling by swabbing, the particulate or sorptively bound soluble substances can be diluted, chemically derivatized and dissolved only after the addition of an external, mostly aqueous solution of the sorption medium, i.e., the swab sampler. Another drawback of this prior-art device is that only a single measurement is possible with the same device due to the swab sampler with the swab sample being directly coupled with the analytical test unit.

SUMMARY AND OBJECTS OF THE INVENTION

Thus, the primary object of the present invention is to provide an improved device for taking swab samples and sample dilution, which does not require the addition of a solution from 15 an additional external reservoir, unlike the prior-art devices, and makes possible a plurality of simultaneous detection tests.

According to the invention a device is provided for taking swab samples and sample dilution. The device has a plug made of a porous, absorbent material, which projects from a sleeve and is used to take a swab sample. The plug is located in one end of the sleeve. A piston, which can be moved in the sleeve by means of a piston rod, is located in the other end of the sleeve. A closure, which can be opened by means of pressure, is located between the piston and the plug, so that a liquid arranged between the piston and the plug moves through the closure to the plug and wets same on actuation of the piston rod.

A detachable piston securing means may be arranged between the sleeve and the grip of the piston rod. This is so the piston rod can be actuated only after removal of the securing means. The sleeve may be transparent and may be provided with markings. The plug may be made of a foam, especially polyurethane, polyethylene, polyester and/or polyether or natural fibers, especially cellulose- or keratin-containing fibers. The liquid may be an aqueous or alcohol solution or suspension.

One essential advantage of the present invention is due to the fact that the same swab sample can be applied to different analytical test units or detection systems, e.g., test strips, one after the other, so that a plurality of different analyses can be performed with one swab sample.

One exemplary embodiment of the present invention will be explained below on the basis of the only FIGURE.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a longitudinal sectional view through a device according to the present invention.

DESCRIPTION OF THE PREFERRED EMBODIMENT

Referring to the drawings in particular, a piston 4, which can be displaced by means of a grip 5 with a piston rod 3, and which sealingly and displaceably fills out the inner cross section of the sleeve 1, is located in a sleeve 1 made of a preferably transparent plastic with markings. An outwardly projecting plug 2 made of a porous and absorbent material, which is provided for taking up the sample to be tested by swabbing a correspondingly covered surface, is located in one end of the sleeve 1. Suitable materials for the plug for taking up the samples are, in particular, chemically inert foams, preferably those made of polyurethane, polyester and/or polyether, but other porous and absorbent materials, e.g., fiber materials made of viscose or cellulose acetate, may be considered as well. A closure 7, which can be opened onto the liquid 6 by means of pressure, is located between the piston 4 and the plug 2, dividing the sleeve into a first chamber 9 and a second chamber 10. The closure is formed so that the liquid 6 moves through the closure 7 toward the plug 2 during the movement of the piston rod 3 in the direction of the plug 2, the liquid is absorbed by the plug and thus it moistens the plug. The closure 7 may comprise, in particular, a membrane that can be opened by pressure and/or include a needle 11. The liquid 6 is, e.g., an aqueous or alcohol rinsing, diluting or formulating solution or suspension, which is used to take up and dissolve the sample to be detected and to subsequently feed it to an analytical detection unit, especially a separate test strip.

To take a swab sample, the contaminated or coated surface is swabbed with the part of the plug 2 projecting on the right in the FIGURE, while the sample to be analyzed is taken up by the porous, absorbent material of the plug 2.

For the analysis, the detachable piston securing means 8 is removed and the liquid 6 can now be delivered into the plug 2 through the closure 7 by pushing in the piston 4. The sample collected on the plug 2 is now rinsed and diluted and can be fed by dropping or dabbing to the analytical detection unit or detection units, especially test strips.

One advantage of the present invention is due to the fact that the sample swabbed is prepared for the subsequent analysis directly by means of a single device and contamination due to preparation with additional external auxiliary means, e.g., pipetting or other laboratory apparatuses, can thus be avoided. Handling is also very simple, because no additional auxiliary means are needed and the sampling, preparation and analysis can be carried out at the sampling site.

While a specific embodiment of the invention has been shown and described in detail to illustrate the application of the principles of the invention, it will be understood that the invention may be embodied otherwise without departing from such principles.

What is clamed is:

1. A device for taking swab samples and sample dilution, the device comprising:
   a sleeve;
   a plug made of a porous, absorbent material, said plug projecting from said sleeve and being used to take a swab sample, said plug being located in one end of said sleeve;
   a piston rod;
   a piston, which can be moved in said sleeve by means of said piston rod, said piston being located in another end of said sleeve;
   a closure, which can be opened by pressure applied thereto, said closure being located between said piston and said plug, said closure divides said sleeve into first and second chambers, said piston is arranged with said first chamber and said plug is arranged with said second chamber, said closure includes a needle extending into said second chamber;
   a liquid arranged between said piston and said plug, said liquid moving through said closure to said plug and wetting same on actuation of said piston rod.

2. The device in accordance with claim 1, further comprising detachable piston securing device arranged between said sleeve and a grip of said piston rod whereby said piston rod can be actuated only after removal of said securing device.

3. The device in accordance with claim 1, wherein said sleeve is transparent and is provided with markings.

4. The device in accordance with claim 2, wherein said sleeve is transparent and is provided with markings.

5. The device in accordance with claim 1, wherein said plug is formed of a foam.

6. The device in accordance with claim 5, wherein said foam is polyurethane, polyethylene, polyester and/or polyether or natural fibers.

7. The device in accordance with claim 1, wherein said plug is formed of natural fibers including cellulose- or keratin-containing fibers.

8. The device in accordance with claim 2, wherein said plug is formed of a foam.

9. The device in accordance with claim 8, wherein said foam is polyurethane, polyethylene, polyester and/or polyether or natural fibers.

10. The device in accordance with claim 2, wherein said plug is formed of natural fibers including cellulose- or keratin-containing fibers.

11. The device in accordance with claim 1, wherein said liquid is an aqueous or alcohol solution or suspension.

12. The device in accordance with claim 2, wherein said liquid is an aqueous or alcohol solution or suspension.

13. The device in accordance with claim 3, wherein said liquid is an aqueous or alcohol solution or suspension.

14. The device in accordance with claim 1, wherein:
   said liquid is a rinsing solution for predetermined contaminants.

15. The device in accordance with claim 1, wherein:
   said liquid is a dissolving solution for predetermined contaminants.

* * * * *